United States Patent [19]

Metzger et al.

[11] Patent Number: 5,145,853

[45] Date of Patent: Sep. 8, 1992

[54] BACTERICIDAL FORMULATIONS FOR USE IN VETERINARY MEDICINE

[75] Inventors: Karl G. Metzger, Wuppertal; Hans-Joachim Zeiler, Velbert; Martin Scheer, Wuppertal; Herbert Voege, Leverkusen; Klaus Grohe, Odenthal, all of Fed. Rep. of Germany

[73] Assignee: Bayer Aktiengesellschaft, Leverkusen, Fed. Rep. of Germany

[21] Appl. No.: 635,817

[22] Filed: Jan. 2, 1991

Related U.S. Application Data

[63] Continuation of Ser. No. 884,708, Jul. 11, 1986, abandoned.

[30] Foreign Application Priority Data

Jul. 24, 1985 [DE] Fed. Rep. of Germany ....... 3526445
Mar. 15, 1986 [DE] Fed. Rep. of Germany ....... 3608745

[51] Int. Cl.$^5$ .................. A61K 31/495; A61K 31/50
[52] U.S. Cl. ...................................... 514/254; 514/247
[58] Field of Search .............................. 514/247, 254

[56] References Cited

U.S. PATENT DOCUMENTS

| | | | |
|---|---|---|---|
| 4,556,658 | 12/1985 | Grohe et al. | 514/254 |
| 4,563,459 | 1/1986 | Grohe et al. | 514/254 |
| 4,659,603 | 4/1987 | Grohe et al. | 514/254 |
| 4,670,444 | 6/1987 | Grohe et al. | 514/254 |
| 4,705,788 | 11/1987 | Schriewer et al. | 514/254 |
| 4,705,789 | 11/1987 | Grohe et al. | 514/254 |

FOREIGN PATENT DOCUMENTS

| | | |
|---|---|---|
| 863429 | 5/1978 | Belgium . |
| 870576 | 3/1979 | Belgium . |
| 0047005 | 3/1982 | European Pat. Off. . |
| 0009425 | 4/1982 | European Pat. Off. . |
| 0049355 | 4/1982 | European Pat. Off. . |

OTHER PUBLICATIONS

Antimicrobial Agents and Chemotherapy, Mar. 1983, vol. 23, No. 3, pp. 509–511.
J. Antimicrob. Chemother. vol. 15, (1985), pp. 787–789.
J. Chromatogr. Biomed. Appl. vol. 339, (1985), pp. 214–218.
Chemotherapy (Tokyo) vol. 32, Suppl. 3, Apr. 1984, pp. 70–85.
Antimicrobial Agents and Chemotherapy, May 1983, vol. 23, No. 5 pp. 641–648.

Primary Examiner—Frederick E. Waddell
Assistant Examiner—Kimberly R. Jordan
Attorney, Agent, or Firm—Sprung, Horn Kramer & Woods

[57] ABSTRACT

A method of treating livestock infected with, or protecting livestock against infection from, bacteria which comprises administering to such livestock an antibacterially effective amount of a quinolonecarboxylic acid or derivative of the formula

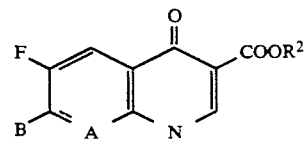

or

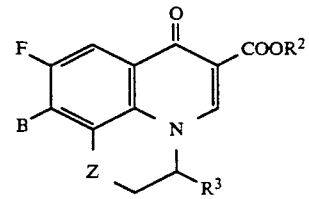

in which
A represents nitrogen or $=C-R^4$,
$R^4$ represents hydrogen, fluorine, chlorine, nitro or methyl,
B represents

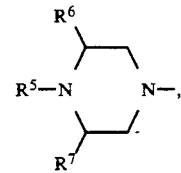

and B also represents

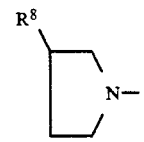

when $R^1$ does not denote cyclopropyl, and
$R^5$ represents hydrogen, a branched or unbranched alkyl group which has 1 to 4 carbon atoms and which can optionally be substituted by a hydroxyl or methoxy group,
$R^6$ represents hydrogen, methyl or phenyl,
$R^7$ represents hydrogen or methyl,
$R^8$ represents amino, alkyl- or dialkylamino having 1 or 2 carbon atoms in the alkyl group, aminomethyl, alkyl- or dialkylaminomethyl having 1 or 2 carbon atoms in the alkyl group,
$R^1$ represents an alkyl radical having 1 to 3 carbon atoms, cyclopropyl, 2-fluoroethyl vinyl, methoxy, 4-fluorophenyl or methylamino,
$R^2$ represents hydrogen, alkyl having 1 to 6 carbon atoms, and cyclohexyl, benzyl, 2-oxopropyl, phenacyl and ethoxycarbonylmethyl,
$R^3$ represents hydrogen, methyl or ethyl, Z represents oxygen, nitrogen which is substituted by methyl or phenyl, and $=CH_2-$,
or a pharmaceutically utilizable salt thereof.

6 Claims, No Drawings

BACTERICIDAL FORMULATIONS FOR USE IN VETERINARY MEDICINE

This application is a continuation of application Ser. No. 884,708, filed Jul. 11, 1986, now abandoned.

The present invention relates to bactericidal formulations which contain quinolonecarboxylic acids and their derivatives, for use in the area of veterinary medicine.

It has already been disclosed that quinolonecarboxylic acids and their derivatives have bactericidal properties (U.S. Ser. No. 614,923, filed May 29, 1984, now pending, corresponding to DE OS 3,033,157). However, nothing has been disclosed about their wide and universal applicability for livestock or about formulations which are especially suitable for applicability for livestock.

In animal medicine the treatment of infections caused by *Escherichia coli,* salmonellae or mycoplasmas present particular problems, especially when these causative organisms have meanwhile become resistant to known agents.

Bactericidal formulations for use in the area of veterinary medicine have been found, which formulations contain quinolonecarboxylic acids and their derivatives of the formulae I and Ia

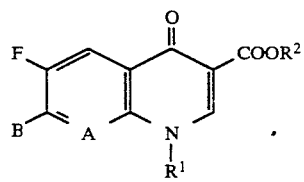
(I)

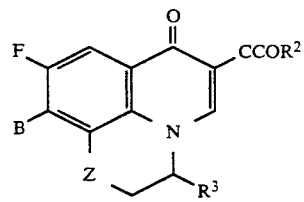
(Ia)

in which
A represents nitrogen or $=C-R^4$,
$R^4$ represents hydrogen, fluorine, chlorine, nitro or methyl,
B represents

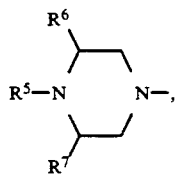

and B also represents

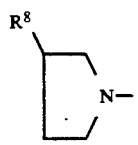

when $R^1$ does not denote cyclopropyl, and
$R^5$ represents hydrogen, a branched or unbranched alkyl group which has 1 to 4 carbon atoms and which can optionally be substituted by a hydroxyl or methoxy group,
$R^6$ represents hydrogen, methyl or phenyl,
$R^7$ represents hydrogen or methyl,
$R^8$ represents amino, alkyl- or dialkylamino having 1 to 2 carbon atoms in the alkyl group, aminomethyl, alkyl- or dialkylaminomethyl having 1 or 2 carbon atoms in the alkyl group,
$R^1$ represents an alkyl radical having 1 to 3 carbon atoms, cyclopropyl, 2-fluoroethyl, vinyl, methoxy, 4-fluorophenyl or methylamino,
$R^2$ represents hydrogen, alkyl having 1 to 6 carbon atoms, and cyclohexyl, benzyl, 2-oxopropyl, phenacyl and ethoxycarbonylmethyl,
$R^3$ represents hydrogen, methyl or ethyl,
Z represents oxygen, nitrogen which is substituted by methyl or phenyl, and $=CH_2-$,
and their pharmaceutically utilizable salts.

The preferred active compounds are quinolonecarboxylic acids and their derivatives of the formula (IIa)

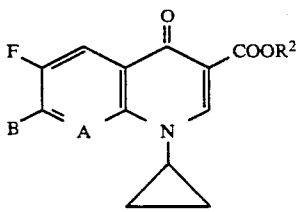
(IIa)

in which
B represents

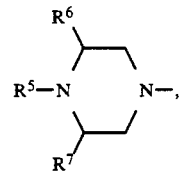

and A, $R^2$, $R^5$, $R^6$ and $R^7$ have the abovementioned meanings.

Particularly preferred active compounds are quinolonecarboxylic acids and their derivatives of the formula (IIa)

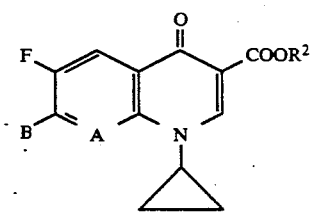
(IIa)

in which
$R^2$ represents hydrogen, alkyl having 1 to 4 carbon atoms, and benzyl, 2-oxopropyl, phenacyl and ethoxycarbonylmethyl,
B represents

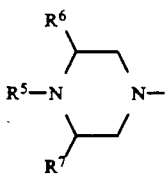

$R^5$ represents hydrogen, methyl or ethyl,
$R^6$ represents hydrogen or methyl,
$R^7$ represents hydrogen or methyl, and
A has the abovementioned meaning.

The following quinolonecarboxylic acids and their derivatives may be especially mentioned as active compounds:

1-cyclopropyl-6-fluoro-1,4-dihydro-4-oxo-7-(1-piperazinyl or 4-methyl- or 4-ethyl-1-piperazinyl-)quinoline-3-carboxylic acid, 1-ethyl-6-fluoro-1,4-dihydro-4-oxo-7-(4-methyl-1-piperazinyl)-quinoline-3-carboxylic acid, 1-ethyl-6-fluoro-1,4-dihydro-4-oxo-7-(1-piperazinyl)-quinoline-3-carboxylic acid, 1-ethyl-6-fluoro-1,4-dihydro-4-oxo-7-(1-piperazinyl)-1,8-naphthyridine-3-carboxylic acid, 9-fluoro-3-methyl-10-(4-methyl-1-piperazinyl)-7-oxo-2,3-dihydro-7,4-pyrido[1,2,4-de]1,4-benzoxazine-6-carboxylic acid, and the methyl and ethyl esters of these compounds.

Pharmaceutically utilizable salts which may be mentioned are salts with acids and bases which form physiologically tolerated salts. The salts are known or can be prepared in analogy to known processes.

Acids which may be mentioned are: hydrochloric acid, sulphuric acid, phosphoric acid, organic acids such as formic acid, acetic acid, lactic acid, maleic acid, fumaric acid, citric acid, ascorbic acid, succinic acid, tartaric acid, malonic acid, maleic acid and embonic acid.

Hydrochloric acid, acetic acid, lactic acid and embonic acid may be mentioned as preferred.

Embonic acid may be mentioned as particularly preferred.

Bases which may be mentioned are inorganic bases such as NaOH, KOH, Ca(OH)$_2$, ammonia, and organic bases such as amines, such as mono-, di- and trialkylamines, substituted amines such as ethanolamine, cyclic amines such as morpholine and piperazine, basic amino acids such as arginine, lysine, choline and N-methylglucamine.

The following bases are preferred: NaOH, KOH, ethanolamine, lysine and N-methylglucamine.

The following bases are particularly preferred: NaOH and KOH.

The active compounds are known or can be prepared in analogy to known processes.

The active compounds are used in the form of formulations suitable for livestock.

Formulations suitable for livestock are:

Solutions such as solutions for injection or oral solutions, concentrates for oral administration after dilution, solutions for use on the skin or in body cavities, pour-on formulations and gels;

emulsions and suspensions for oral or cutaneous use and for injection; semisolid formulations;

formulations in which the active compound is incorporated into an ointment base or into an oil-in-water or water-in-oil emulsion base;

solid formulations such as powders, premixes or concentrates, granules, pellets, tablets, boli, capsules; aerosols and inhalants.

Solutions for injection are administered intravenously, intramuscularly and subcutaneously.

Solutions for injection are prepared by dissolution of the active compound in a suitable solvent and possibly addition of additives such as solubilizers, acids, bases, buffer salts, antioxidants and preservatives. The solutions are sterilized by filtration and dispensed into containers.

Solvents which may be mentioned are: physiologically tolerated solvents such as water, alcohols such as ethanol, butanol, benzyl alcohol, glycerol, propylene glycol, and polyethylene glycols, and N-methyl-pyrrolidone, and mixtures thereof.

The active compounds can, where appropriate, also be dissolved in physiologically tolerated vegetable or synthetic oils which are suitable for injection.

Solubilizers which may be mentioned are: solvents which promote the dissolution of the active compound in the main solvent or prevent its precipitation. Examples are polyvinylpyrrolidone, polyoxyethylated castor oil and polyoxyethylated sorbitan esters.

Preservatives are: benzyl alcohol, trichlorobutanol, p-hydroxybenzoic esters and n-butanol.

Oral solutions are used directly. Concentrates are used orally after previous dilution to the use concentration. Oral solutions and concentrates are prepared as described above for the solutions for injection, it being possible to dispense with sterile working.

Solutions for use on the skin or in body cavities are applied dropwise, by painting on, rubbing in or spraying on, or in dips. These solutions are prepared as described above for the solutions for injection. It is particularly advantageous to add thickening agents during preparation.

Thickening agents are: inorganic thickening agents such as bentonites, colloidal silica and aluminium monostearate, and organic thickening agents such as cellulose derivatives, polyvinyl alcohols and their copolymers, acrylates and metacrylates.

Gels are applied to or smeared on the skin or introduced into body cavities. Gels are prepared by mixing solutions, which have been prepared as described for the solutions for injection, with sufficient thickening agent to produce a clear composition with an ointment-like consistency. The thickening agents which are used are the abovementioned thickening agents.

Pour-on formulations are poured or sprayed onto limited areas of the skin, the active compound either penetrating through the skin and acting systemically or distributing itself on the body surface.

Pour-on formulations are prepared by dissolution, suspension or emulsion of the active compound in suitable solvents or solvent mixtures which are tolerated by skin. Where appropriate, further auxiliaries, such as pigments, substances promoting absorption, antioxidants, sunscreen agents and adhesion promoters, are added.

Solvents which may be mentioned are: water, alkanols, glycols, polyethylene glycols, polypropylene glycols, glycerol and aromatic alcohols, such as benzyl alcohol, phenylethanol and phenoxyethanol, esters, such as ethyl acetate, butyl acetate and benzyl benzoate, ethers such as alkylene glycol alkyl ethers, such as dipropylene glycol monomethyl ether and diethylene glycol mono-butyl ether, ketones such as acetone and methyl ethyl ketone, aromatic and/or aliphatic hydrocarbons, vegetable or synthetic oils, DMF, dimethylacetamide, N-methylpyrrolidone and 2-dimethyl-4-oxymethylene-1,3-dioxolane.

Pigments are all pigments which are approved for use on livestock and which can be dissolved or suspended.

Substances promoting absorption are DMSO, spreading oils, such as isopropyl myristate, dipropylene glycol pelargonate, silicone oils, fatty acid esters, triglycerides and fatty alcohols.

Antioxidants are sulphites or metabisulphites, such as potassium metabisulphite, ascorbic acid, butylhydroxytoluene, butylhydroxyanisole and tocopherol.

Examples of sunscreen agents are substances from the class of benzophenones or novantisol acid.

Examples of adhesion promoters are cellulose derivatives, starch derivatives, polyacrylates, and natural polymers such as alginates and gelatin.

Emulsions can be used orally, cutaneously or as injections.

Emulsions are either of the water-in-oil type or of the oil-in-water type.

They are prepared by dissolution of the active compound in one phase and homogenization thereof with the aid of suitable emulsifiers and, where appropriate, further auxiliaries, such as pigments, substances promoting absorption, preservatives, antioxidants, sunscreen agents and substances increasing the viscosity.

The following may be mentioned as the hydrophobic phase (oils): paraffin oils, silicone oils, natural vegetable oils such as sesame oil, almond oil and caster oil, synthetic triglycerides such as caprylic/capric acid biglyceride, triglyceride mixture with vegetable fatty acids of chain length $C_{8-12}$, or other specially selected natural fatty acids, partial glyceride mixtures of saturated or unsaturated fatty acids which possibly also contain hydroxyl group, and mono- and diglycerides of $C_8/C_{10}$- fatty acids.

Fatty acid esters such as ethyl stearate, di-n-butyryl adipate, hexyl laurate, dipropylene glycol pelargonate, esters of a branched fatty acid of medium chain length with saturated fatty alcohols of chain length $C_{16}$–$C_{18}$, isopropyl-myristate, isopropyl palmitate, caprylic/capric esters of saturated fatty alcohols of chain length $C_{12}$–$C_{18}$, isopropyl stearate, oleyl oleate, decyl oleate, ethyl oleate, ethyl lactate, wax-like fatty acid esters such as artificial duck preen gland fat, dibutyl phthalate, diisopropyl adipate, ester mixtures related to the latter, etc.

Fatty alcohols such as isotridecyl alcohol, 2-octyldodecanol, cetylstearyl alcohol, oleyl alcohol.

Fatty acids such as, for example, oleic acid and its mixtures.

The following may be mentioned as hydrophilic phase: water, alcohols such as, for example, propylene glycol, glycerol, sorbitol and their mixtures.

Emulsifiers which may be mentioned are: surfactants (including emulsifiers and wetting agents), such as
1. non-ionic, for example polyoxyethylated castor oil, polyoxyethylated sorbitan monooleate, sorbitan monostearate, ethyl alcohol, glycerol monostearate, polyoxyethyl stearate, alkylphenol polyglycol ethers,
2. ampholytic such as di-Na N-lauryl-$\beta$-iminodipropionate or lecithin,
3. anionic such as Na lauryl sulphate, fatty alcohol ether sulphates, mono/dialkyl polyglycol ether orthophosphate monoethanolamine salt,
4. cationic such as cetyltrimethylammonium chloride.

Other suitable auxiliaries are: substances which increase the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica or mixtures of the substances listed.

Suspensions can be used orally, cutaneously or as injection. They are prepared by suspension of the active compound in a liquid vehicle, where appropriate with the addition of further auxiliaries, such as wetting agents, pigments, substances promoting absorption, preservatives, antioxidants and sunscreen agents.

Liquid vehicles which may be mentioned are all homogeneous solvents and solvent mixtures.

The following may be mentioned as wetting agents (dispersing agents):

Surfactants (including emulsifiers and wetting agents) such as
1. anionic, such as Na lauryl sulphate, fatty alcohol ether sulphates, mono/dialkyl polyglycol ether orthophosphate monoethanolamine salt, ligninsulphonates or dioctyl sulphosuccinate,
2. cationic, such as cetyl trimethylammonium chloride,
3. ampholytic, such as di-Na N-lauryl-$\beta$-iminodipropionate or lecithin
4. non-ionic, for example polyoxyethylated castor oil, polyoxyethylated sorbitan monooleate, sorbitan monostearate, ethyl alcohol, glycerol monostearate, polyoxyethylene stearate, alkylphenol polyglycol ethers, and Pluronic ®.

The further auxiliaries which may be mentioned are those indicated above.

Semisolid formulations can be administered orally or cutaneously. They differ from the suspensions and emulsions which are described above only by their higher viscosity.

For the preparation of solid formulations, the active compound is mixed with suitable vehicles, where appropriate with the addition of auxiliaries, and converted into the desired shape.

Vehicles which may be mentioned are all physiologically tolerated, solid, inert substances. All such serve inorganic and organic substances. Examples of inorganic substances are sodium chloride, carbonates such as calcium carbonate, bicarbonates, aluminum oxides, silicas, aluminas, precipitated or colloidal silicon dioxide, and phosphates.

Examples of organic substances are sugars, cellulose, foodstuffs and feedstuffs such as powdered milk, meat-and-bone meals, coarse and fine grain meals and starches.

Auxiliaries are preservatives, antioxidants and pigments, which have already been listed above.

Other suitable auxiliaries are lubricating agents, and lubricants such as, for example, magnesium stearate, stearic acid, talc and bentonites, substances promoting disintegration, such as starch or crosslinked polyvinylpyrrolidone, binders such as, for example, starch, gelatin or linear polyvinylpyrrolidone, and dry binders such as microcrystalline cellulose.

The active compounds can also be encapsulated in the form of their abovementioned solid or liquid formulations.

The active compounds can also be used in the form of an aerosol. For this purpose, the active compound is finely divided in a suitable formulation under pressure.

It may also be advantageous to use the active compounds in formulations which release the active compound in a delayed manner.

The active compounds are preferably administered together with the feed and/or the drinking water.

The feed includes non-compound feedstuffs of vegetable origin, such as hay, roots, grain, grain byproducts, non-compound feedstuffs of animal origin, such as meat, fats, milk products, bonemeal and fish products, also the non-compound feedstuffs such as vitamins, proteins, amino acids, for example DL-methionine, and salts such as lime and sodium chloride. The feed also includes supplementary, compound and mixed feedstuffs. These containing non-compound feedstuffs in a composition which ensures a balanced diet in respect of the supply of energy and protein and the supply of vitamins, mineral salts and trace elements.

The concentration of the active compounds in the feed is normally about 0.01-500 ppm, preferably 0.1-50 ppm.

The active compounds can be added as such, or in the form of premixes or feed concentrates, to the feed.

Premixes and feed concentrates are mixtures of the active compound with a suitable vehicle.

The vehicles include the non-compound feedstuffs or mixtures thereof.

Furthermore, they can contain further auxiliaries such as, for example, substances which control the flow properties and miscibility, such as, for example, silicas, bentonites and ligninsulphonates. Furthermore, it is possible to add antioxidants such as BHT or preservatives such as sorbic acid or calcium propionate.

Concentrates for administration in the drinking water must be formulated so that a clear solution or a stable homogeneous suspension is produced on mixing with the drinking water.

Thus, suitable vehicles are substances which are soluble in water (feed additives) such as sugars or salts (for example citrates, phosphates, sodium chloride and Na carbonate).

They may likewise contain antioxidants and preservatives.

The active compounds can be present in the formulations alone or mixed with other active compounds, mineral salts, trace elements, vitamins, proteins, pigments, fats or flavorings.

The active compounds are active against microorganisms pathogenic to livestock.

The microorganisms pathogenic to livestock include:
1. Spirochaetaceae (for example Treponema, Leptospira and Borrelia)
2. Spirillaceae
3. Micrococcaceae (for example Staphylococci biotype A-F, St. hyicus)
4. Streptococcaceae (for example *Streptococcus uberis*, Str. equi, Str. agalactiae, Str. dysgalactiae, Streptococci of Lancefield types A-N)
5. Pseudomonaceae (for example *Pseudomonas malei, Ps. cepacia., Ps, aeruginosa* and *Ps. maltophilia*), Brucella such as *Brucella abort., B. melitensis* and *B. suis*, Bordetella such as *Bordetella bronchiseptica,* Moraxella and Acinetobacter)
6. Enterobacteriaceae (for example Salmonella of types B-E, Shigella, *E. coli,* Klebsiella, Proteus, Citrobacter, Edwardsiella, Haemophilus, Providencia and Yersina)
7. Vibrionaceae (for example Vibrio such as Vibrio cholerae, Pasteurella such as *Pasteurella multocida,* Aeromonas, Actinobacillus and Streptobacillus)
8. Bacetroidaceae (for example Bacteroides and Fusobacterium)
9. Lactobacillaceae (Erysiphylothrix, Listeria such as *Listeria monocytojenes*)
10. Bacillaceae (for example Bacillus, Clostridium types A-D, such as *Clostridium perfringens*) and Lactobacillaceae, and anaerobic Cocci such as, for example, Peptostreptococci and Peptococci
11. Coryneform bacteria (for example *Corynebacterium pyoenes*)
12. Mycobacteriacease (for example *Mycobacterium bovis, M. avium* and *M. tuberculosis*)
13. Actinomyceae (for example *Actinomyces bovis* and *A. israelii*)
14. Nocardiaceae (for example *Norcardia facinica* and *N. asteroides*)
15. Rickettsiaceae (for example Coxiella and Rickettsia)
16. Bartonellaceae (for example Bartonella)
17. Chlamydiaceae (for example *Mycoplasma mycoides, M. agalactiae* and *M. gallisepticum*).

Microorganisms pathogenaic for livestock can cause, as single or mixed infections, manifestations of disease in the following organ systems of the livestock: stock:

Lung and trachinal space, digestive systems such as stomach and intestine, udder, genital system such as uterus, soft tissues, such as skin, muscles, nails, claws and hooves, active and passive locomotor systems such as bones, muscles, tendons and joints, urogenital systems such as kidneys, ureter and urethra, nervous system, auditory apparatus and eyes.

As already mentioned, the active compounds are used to combat bacterial diseases in livestock. The livestock include:

Mammals, such as, for example, cattle, horses, pigs, sheep, goats, dogs, cats, rabbits, camels, fur-bearing animals such as mink and chinchilla, and animals in zoos and laboratories, such as, for example, mice and rats; reptiles, such as, for example, crocodiles and snakes.
The bacterial diseases include, for example:
in pigs
for example coli diarrhoea, enterotoxaemia and septicaemia, and dysentery, salmonellosis, arthritis, enzootic pneumonia, rhinitis atrophicans, metritismastitis-agalactia syndrome, mastitis and erysipelas; in ruminants
for example (cattle, sheep and goats) coli diarrhoea and septicaemia, bronchopneumonia, salmonellosis, shipping fever, pasteurellosis, mycoplasmosis, puerperal and postpuerperal genital infection, and mastitis; in horses
for example bronchopneumonia, lameness of foals, puerperal and postpuerperal infections, and salmonellosis;
in dogs and cats for example bronchopneumonia, diarrhoes, dermatitis, pyoderma, otitis, urinary tract infections, prostatitis, orchitis and encephalomyelitis;
in poultry (chickens, turkeys, guineafowl, quail, pigeons, ornamental birds etc.) mycoplasmosis, E. coli infections, chronic respiratory disease, salmonellosis, contagious avian influenza, pasteurellosis, Campylobacter infection, and psittacosis-ornithosis; and infections or mixed infections, in the species mentioned and others, with, for example, *Escherichia coli,* Salmonella spp., Klebsielle spp., Proteus spp., Haemophilus spp., Pasteurella spp., Actinobacillus spp., Pseudomonas spp., Brucella spp., ordetella spp., Moraxella spp., Campylobacter spp., Staphylococcus spp., Streptococcus spp., Listeria spp., Erysipelothrix spp., Cornynebacterium spp., Fusobacterium spp., Borellia spp., Treponema spp., Leptospira spp., Clostridium spp., Mycoplasma spp., Nocardia spp., Rickettsia spp., Mycobacterium spp., and Yersinia spp.

Treatments can be carried out as follows, for example:

Diseases in pigs:

Coli diarrhoea of suckling pigs, coli enterotoxaemia of weaned pigs: oral, parenteral or combined oral-parenteral treatment with suitable solid or liquid formulations for oral use or solutions for injection for parenteral use in doses of 0.5 to 10, preferably 1 to 5, mg/kg of body weight, once to twice a day, for 1 to 15, preferably 1 to 3, days.

Salmonelloses, enzoot. pneumonia, rhinitis atrophicans; MMA syndrome, mastitis: treatments as indicated above; alternatively treatment by administration in the feed 50 to 800 mg/kg of feed, preferably 100 to 200, and for sows 100 to 400 mg/kg of feed, for 5 to 20 days, where appropriate repeated (prophylaxis program).

Diseases of ruminants (cattle, sheep and goats):

Coli diarrhoae and septicaemia, bronchopneumonia, salmonellosis, shipping fever, pasteurellosis, mycoplasmosis: oral, parenteral or combined oral-parenteral treatment with boli, solutions (drenches), suspensions, pastes, premix etc. for oral administration, and formulations for injection for parenteral administration, in doses of 1 to 20, preferably 1 to 5, mg/kg of body weight, once to twice a day, for 1 to 15, preferably 1 to 5, days, where appropriate repeated.

Genital infections, mastitis: systemic treatment as above; additionally or alternatively local treatment with suitable formulations, boli, solutions, suspensions, pastes for introduction into body cavities or organis (uterus; ;udder); for example administrations of one or more uterine suppositories, once to several times a day, until the signs have disappeared; infusion of tolerated solutions, suspensions and pastes in the uterus or (1–4) udder quarters, with appropriate repeat treatment depending on the clinical signs.

Disease of horses:

Bronchopneumonia, lameness in foals, peurperal and postpuerperal infections, salmonellosis: oral, parenteral or combined oral-parenteral, preferably parenteral, treatment with suitable formulations, boli, solutions, suspensions, pastes, premix etc., or solutions for injection, for intramuscular, subcutaneous and, preferably, intravenous administration in doses from 1 to 20, preferably 2.5 to 10, mg/kg of body weight, once to twice a day, for 1 to 20, preferably 1 to 10, days, where appropriate repeated. Diseases of small animals, for example dogs and cats: All bacterial diseases: oral, parenteral or combined oral-parenteral, where appropriate local, use with suitable formulations, tablets, solutions, suspensions, pastes and formulations for injection, in doses from 1 to 20, preferably 2.5 to 10, mg/kg of body weight, once to twice a day, for 1 to 30, preferably 1 to 10, days.

Poultry diseases, especially caused by *E. coli*, Mycoplasma, Salmonella, Pasteurella, Campylobacter etc.: oral and/or parenteral treatment with suitable formulations, preferably oral treatment in the drinking water, 10 to 500 mg/l, preferably 2.5 to 100 mg/l, for 1 to 20, preferably 3 to 10, days, where appropriate repeated (prophylaxis programme).

Preparations containing the abovementioned active compounds are particularly suitable for treating infections caused by *E. coli*, salmonellae and/or mycoplasmas. They are particularly suitable for use against those organisms causing infection diseases which have become resistance to currently known agents.

Particular mention may be made of the suitability of preparations containing the abovementioned active compounds for the treatment of salmonelloses and mycoplasma infections in poultry, in particular in hens and fattened hens.

Particular mention may also be made of the suitability of preparations containing the abovementioned active compounds for the treatment of infections caused by mycoplasmas, *E. coli* or salmonellae in pigs, particularly in piglets.

The simple and convenient treatment of salmonella and mycoplasma diseases in poultry, particularly hens, via their feed and drinking water must be particularly emphasized. The treatment via drinking water is preferred. The active compounds are dissolved in the drinking water either in the form of their salts with water-soluble acids or in the form of their salts with water-soluble bases.

For the formation of the salts the bases or acids are added to the active compounds preferably in more than equimolar amounts, so that the ready-to-use aqueous solution is basic- or acid-reacting.

The ready-to-use solutions contain preferably 10–50 ppm, particularly preferably 25–110 ppm and with very particular preference 50–100 ppm of active compound.

The pH value of the ready-to-use acid solution is between 2 and 5, preferably between 3 and 5.

The pH value of the ready-to-use basic solution is between 8 and 11, preferably between 9 and 10.

As already mentioned the abovementioned active compounds are particularly suitable for the treatment via feeds, of infections in pigs caused by E. coli, mycoplasmas and/or salmonellae. For this purpose the active compounds are added to the feed in the form of a premix in such a manner that a medicated animal feed is produced in which the active compound is present in the required concentration.

In this treatment of pigs via their feed the embonates of the abovementioned active compounds are preferably used.

EXAMPLES

In the following examples 1-cyclopropyl-6-fluoro-1,4-dihydro-4-oxo-7(4-ethyl-1-piperazinyl)-quinoline-5-carboxylic acid (I) and 1-cyclopropyl-6-fluoro-1,4-dihydro-4-oxo-7-(1-piperazinyl)-quinoline carboxylic acid (II) are used as the active compounds.

A. General instructions for preparing basic-reacting concentrates for use in drinking water:

The active compound and the auxiliaries are suspended in the greater amount of water. The alkali is added carefully while stirring until the active compound has dissolved. Stirring is continued until a clear, thinly liquid gel has formed which contains no lumps.

EXAMPLE 1

| | |
|---|---|
| Active compound I | 2.500 g |
| Benzyl alcohol | 1.400 g |
| methyl hydroxypropyl-cellulose | 3.500 g |
| potassium hydroxide up to pH 11 | 0.004 g |
| demineralized water | 95.996 g |

|  | 100 ml | 100,900 g |
|---|---|---|

EXAMPLE 2

| Active compound II |  | 2.00 g |
|---|---|---|
| Polyacrylic acid Na-salt |  | 0.62 g |
| Sodium hydroxide solution 1N |  | 12.00 g |
| Benzyl alcohol |  | 1.00 g |
| Demineralized water |  | 85.08 g |
|  | 100 ml | 100.70 g |

EXAMPLE 3

| Active compound I |  | 20.00 g |
|---|---|---|
| Benzyl alcohol |  | 1.00 g |
| 10% potassium hydroxide solution |  | 30.56 g |
| Demineralized water |  | 55.94 g |
|  | 100 ml | 107.50 g |

B. General instructions for preparing acid-reacting concentrates for use in drinking water:

EXAMPLE 4

| Active compound I |  | 10.0 kg |
|---|---|---|
| acetic acid |  | 2.5 kg |
| Benzyl alcohol |  | 1.0 kg |
| Demineralized water |  | 89.7 kg |
|  | 100 l | 103.2 kg |

Water is initially introduced into a vessel and the remaining substances are added with stirring.

EXAMPLE 5

| Active compound II |  | 5.0 kg |
|---|---|---|
| 20% lactic acid |  | 10.0 kg |
| Demineralized water |  | ad 100 l |

The preparation is carried out as described in Example 4.

C. General instructions for preparing premixes for use in feeds:

EXAMPLE 6

| Active Compound I* |  | 10.0 kg |
|---|---|---|
| Wheat nuddlings |  | 88.0 kg |
| precipitated silicic acid |  | 2.0 kg |
|  |  | 100.0 kg |

*in the form of its embonate

The substances are introduced, with weighing, into a mixer and mixed until homogenity is achieved.

EXAMPLE 7

| Active compound I* |  | 5.0 kg |
|---|---|---|
| Calcium carbonate |  | 95.0 kg |
|  |  | 100 kg |

*in the form of its embonate

Calcium carbonate is introduced, with weighing, into a mixer and the active compound is added thereto while mixing the ingredients.

D. General instructions for preparing a ready-to-use feed for pigs:

EXAMPLE 8

1 kg of premix according to Example 6 is initially mixed with 199 kg of a conventional piglet starter. This mixture is added to a further 1800 kg of piglet starter and mixed therewith until homogenity is achieved.

In the following use examples the excellent suitability of the abovementioned active compounds for the treatment of diseases in poultry via their drinking water and in pigs via their feed is demonstrated.

EXAMPLE 1

Treatment of mycoplasmoses in poultry

Groups of 40 chicken which were free from mycoplasma gallisepticum and mycoplasma synoviae were infected at the second day after hatching with a pathogenic wild strain of mycoplasma gallisepticum. The treatment began 24 hours after the infection. One group of 40 chickens was not treated and served as a control. The chickens were treated via their drinking water at 5 successive days following the infection. 19 days after the infection the animals were killed, weighed and examined. The following results were obtained:

TABLE 1

| Drinking water treatment with | Average weight of the animals after | | | clinical symptoms |
|---|---|---|---|---|
|  | 0 | 14 | 19 |  |
| Compound I 250 ppm | 47.3 | 355.7 | 463.8 | none |
| Comparative substance Tylocin 500 ppm | 48.4 | 311.9 | 426.3 | clearly noticeable, no animals dead |
| untreated | 48.2 | 269.6 | 347.4 | clearly noticeable, 18 animals dead |

No mycoplasmas were isolated from any of the treated animals after they had been killed.

EXAMPLE 2

Treatment of salmonella infections in pigs 6 pigs (weight 20–26 kg) were infected with Salmonella (S.) derby orally via their feed, the dosage for infection being 10 ml with a number of organisms of about $10^8$ salmonellae/m. On the 10th day after infection the treatment was begun using feed containing 200 mg/kg of compound I (ad libitum). The duration of the treatment was 5 days.

Up until the 17th day after infection, the excrement of the test animal was examined for salmonellae by means of cultures using 2 enrichment methods (potassium tetrathionate brilliant green lile medium, selenitebroth) and 2 solid selective culture media (water blue metachrome yellow lactose agar according to Gassner, brilliant green phenol read lactose agar according to Kauffmann).

The results are shown in Table II.

TABLE II

Detection of salmonellae in experiments upon experimental infection of piglets after 5-day treatment

| Day of examination after infection | Piglet No. (Infection with S. derby: 10 ml ($10^8$ organism per ml)) | | | | | |
|---|---|---|---|---|---|---|
| | 1 | 2 | 3 | 4 | 5 | 6 |
| 2nd | + | + | + | + | + | + |
| 6th | + | + | + | + | + | + |
| 8th | + | + | + | + | + | + |
| 1st day of treatment | | | | | | |
| 10th | − | − | − | − | − | − |
| 12th | n.e. | n.e. | n.e. | n.e. | n.e. | n.e. |
| last day of treatment | | | | | | |
| 13th | − | − | − | − | − | − |
| 15th | − | − | − | − | − | − |
| 17th | − | − | − | − | − | − |

Explanation:
+ salmonellae detected
− no salmonellae detected
n.e. not examined

EXAMPLE 3

Treatment of mycoplasmoses in pigs

Groups of 5 piglets with an average weight of 25 kg were fed with standard piglet feed from the beginning of the test, to which feed the stated quantities of active compound had been added.

On the 4th day after the beginning of the test, the animals were infected with mycoplasmas mycopneumoniae. As from the 10th day the animals were only given feed not containing any active compound. On the 34th day the animals were killed and the lungs were examined for lesions.

The following results were obtained:

TABLE III

Treatment of mycoplasmoses in pigs

| Concentration of active compound in the feed mg/kg | result |
|---|---|
| Compound I 100 | no lesions |
| Compound I 50 | no lesions |
| Tiamulin 200 | 5% lesions |
| Control without any additives | 10% lesions |

EXAMPLE 4

Mycoplasmas/Inhibitory concentration test

The test was carried out on microtiter plates. Series of concentrations of the active compound in 0.01 N soda solution were prepared. The concentrations were from 256 μg/ml to 0.0156 μg/ml.

0.5 ml of an active compound solution are placed in each identation in the microtiter plate. To this 0.5 ml of an inoculum of mycoplasmas containing about $10^6$ organisms per ml were added.

The inoculum consisted of a modified mycoplasma broth (PPLO) which contained about 20% of horse serum and in which mycoplasmas had been cultured to a titer of about $10^7$ organisms per ml (determined by the MacCrady method).

Then the microtiter plate was incubated at 37° C. and the growth determined after 48, 72 and 96 hours. That concentration of active compound, which prevented any increase in the moculated mycoplasmas was taken as the MIC-value.

TABLE IV

| Active compound | Mycoplasmas/Inhibitory concentration MIC values for mycoplasma strains no. | | | | | |
|---|---|---|---|---|---|---|
| | 348 | 7981 | 6442 | 4587 | 81115 | 8008 |
| Compound I | 0.5 | 0.5 | 0.15 | 0.5 | 0.5 | 0.25 |
| Comparative substance: nalidixic acid | 128 | 128 | 128 | 128 | 128 | 128 |
| flumequine | 256 | 256 | 256 | 256 | 256 | 256 |

It will be understood that the specification and examples are illustrative but not limitative of the present invention and that other embodiments within the spirit and scope of the invention will suggest themselves to those skilled in the art.

We claim:

1. A method of treating mycoplasmotic and bacterial infections in fowl which comprises administering drinking water to said fowl, said drinking water containing an antimycoplasmotically or antibacterially effective amount of a quinolonecarboxylic acid and/or derivative of a compound of the formula

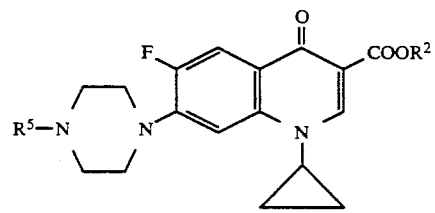

in which
$R^2$ represents hydrogen or $C_{1-4}$-alkyl and
$R^5$ represents hydrogen, methyl or ethyl.

2. A method according to claim 1, wherein 10 to 500 mg/l of the compound is added to said drinking water for 1 to 20 days.

3. A method according to claim 2, wherein 2.5 to 100 mg/l of the compound is added to said drinking water.

4. A method according to claim 2, wherein said compound is added to said drinking water for 3 to 10 days.

5. A method according to claim 1, wherein said fowl are hens.

6. A method according to claim 1, wherein said compound is 1-cyclopropyl-6-fluoro-1,4-dihydro-4-oxo-7 (4-ethyl-1-piperazinyl) quinoline-3-carboxylic acid.

* * * * *